US007387998B2

(12) United States Patent
Brooks et al.

(10) Patent No.: US 7,387,998 B2
(45) Date of Patent: Jun. 17, 2008

(54) STQ PEPTIDES

(75) Inventors: Peter C. Brooks, Carmel, NY (US); Abebe Akalu, New York, NY (US)

(73) Assignee: New York University, New York, NY (US)

( * ) Notice: Subject to any disclaimer, the term of this patent is extended or adjusted under 35 U.S.C. 154(b) by 251 days.

(21) Appl. No.: 10/797,626

(22) Filed: Mar. 9, 2004

(65) Prior Publication Data
US 2004/0224896 A1 Nov. 11, 2004

Related U.S. Application Data

(60) Provisional application No. 60/458,523, filed on Mar. 28, 2003.

(51) Int. Cl.
*A61K 38/00* (2006.01)
*A61K 38/04* (2006.01)

(52) U.S. Cl. .................. 514/15; 530/326; 530/327; 514/15

(58) Field of Classification Search .............. None
See application file for complete search history.

(56) References Cited

U.S. PATENT DOCUMENTS

| 5,092,885 | A | 3/1992 | Yamada et al. | |
|---|---|---|---|---|
| 5,112,946 | A | 5/1992 | Maione | |
| 5,192,744 | A | 3/1993 | Bouck et al. | |
| 5,202,352 | A | 4/1993 | Okada et al. | |
| 6,071,520 | A * | 6/2000 | Noteborn et al. | 424/186.1 |
| 7,122,635 | B2 | 10/2006 | Brooks et al. | |
| 2004/0224896 | A1 | 11/2004 | Brooks | |

FOREIGN PATENT DOCUMENTS

| WO | WO 00/40597 | 7/2000 |
|---|---|---|
| WO | WO-00-59532 A1 | 10/2000 |

OTHER PUBLICATIONS

Amstutz, et al., In vitro display technologies: novel developments and applications. Current Opinion in Biotechnology 2001;12:400-405.
Blood, et al., Biochim. Biophys. Acta. 1990;1032:89-118.
Brooks, et al., J Clin. Invest. 1995;96:1815-1822.
Brooks, et al., Cell 1994;79:1157-1164.
Brooks, et al., Cell 1998;92:391-400.
Green, et al., Proc. Natl. Acad. Sci. USA 2003;100:1010-1015.
Guo, et al., In vitro evolution of amphioxus insulin-like peptide to mammalian insulin. Biochemistry 2002;41:10603-10607.
Hangai, et al., Matrix metalloproteinase-9-dependent exposure of a cryptic migratory control site in collagen is required before retinal angiogenesis. American Journal of Pathology 2002;161(4):1429-1437.
Heeley RP, Endocr. Res. 2002;28:217-229.
Kurschat, et al., Clin. Exp. Dermatol. 2000;25:482-489.
Liljeblad, et al., Analysis of agalacto-IgG in rheumatoid arthritis using surface plasmon resonance. Glycoconjugate Journal 2000;17:323-329.
Liotta, et al., Cell 1991;64:327-336.
Roskelly, et al., Curr. Op. Cell Biol. 1995;7:736-747.
Stephanopoulos G, Metabolic engineering by genome shuffling. Nature Biotechnology 2002;20(7):666-668.
Tani, et al., In vitro selection o fibronectin gain-of-function mutations. Biochem. J. 2002;365:287-294.
Varner, et al., Cell Adh. Commun. 1995;3:367-374.
Xu, et al., Generation of monoclonal antibodies to cryptic collagen sites by using subtractive immunization. Hybridoma 2000;19(5)375-385.
Xu, et al., Proteolytic exposure of a cryptic site within collagen type IV is required for angiogenesis and tumor growth in vivo. Journal of Cell Biology 2001;154(5):1069-1079.
Weidner, et al., J. Natl. Cancer Inst. 1992;84:1875-1887.
Weidner, et al., N. Engl. J Med. 1991;324:1-7.
Wyckoff, et al., Cancer Res. 2000;60:2504-2511.
Akalu , A. et al., "Inhibition of angiogenesis and tumor metastasis by targeting a matrix immobilized cryptic extracellular matrix epitope in laminin," Cancer Res. 67(9):4353-4363 (2007).
Gonzalez, A. et al., "Complex interactions between the laminin alpha 4 subunit and integrins egulate endothelial cell behavior in vitro and angiogenesis in vivo," PNAS USA 99(25):16075-16080 (2002).
Kikkawa, Y. et al., "Isolation and characterization of laminin-10/11 secreted by human lung carcinoma cells. Laminin-10/11 mediates cell adhesion through integrin alpha3 beta1," J. Biol. Chem. (online), Am. Soc. Biochem. Mol. Biol., 273 (25):15854-15859 (1998).
Kurkinen, M. et al., "In vitro synthesis of laminin and entactin polypeptides," J. Biol. Chem. 258(10):6543-6548 (1983).
EP04758409.9 Supp EP Search Report dated Jul. 19, 2007.

* cited by examiner

*Primary Examiner*—Cecilia Tsang
*Assistant Examiner*—Thomas S Heard
(74) *Attorney, Agent, or Firm*—Wilson Sonsini Goodrich & Rosati

(57) ABSTRACT

The invention describes methods for inhibiting angiogenesis in a tissue by administering an antagonist that specifically binds to a proteolyzed or denatured laminin with substantially greater affinity than to the native form of laminin. Methods utilizing such antagonists for therapeutic treatment of tumor growth, tumor metastasis or of restenosis also are described, as are methods to use such antagonists as diagnostic markers of angiogenesis in normal or diseased tissues both in vivo and ex vivo.

3 Claims, 5 Drawing Sheets

SEQUENCE LISTING

```
<160> NUMBER OF SEQ ID NOS: 3

<210> SEQ ID NO 1
<211> LENGTH: 13
<212> TYPE: PRT
<213> ORGANISM: artificial sequence
<220> FEATURE:
<223> OTHER INFORMATION: denatured laminin selective antagonist

<400> SEQUENCE: 1

Ser Thr Gln Asn Ala Ser Leu Leu Ser Leu Thr Val Cys
1               5                   10

<210> SEQ ID NO 2
<211> LENGTH: 19
<212> TYPE: PRT
<213> ORGANISM: artificial sequence
<220> FEATURE:
<223> OTHER INFORMATION: denatured laminin selective antagonist

<400> SEQUENCE: 2

Lys Gly Gly Cys Ser Thr Gln Asn Ala Gln Leu Leu Ser Leu Ile Val
1               5                   10                  15

Gly Lys Ala

<210> SEQ ID NO 3
<211> LENGTH: 18
<212> TYPE: PRT
<213> ORGANISM: artificial sequence
<220> FEATURE:
<223> OTHER INFORMATION: denatured laminin selective antagonist

<400> SEQUENCE: 3

Lys Gly Gly Ser Thr Gln Asn Ala Gln Leu Leu Ser Leu Ile Val Gly
1               5                   10                  15

Lys Ala
```

US 7,387,998 B2

STQ PEPTIDES

This application claims priority under 35 U.S.C. §119(e) to U.S. provisional application Serial No. 60/458,523 filed on Mar. 28, 2003. The contents of this provisional application are hereby incorporated by reference in their entirety.

FIELD OF THE INVENTION

This invention relates generally to the field of medicine, and more specifically to methods and compositions for inhibiting or detecting angiogenesis, tumor growth and metastases using active agents comprising selective antagonists of denatured laminin.

BACKGROUND

Tumor growth and metastasis impact a large number of people each year. It is estimated that over 600,000 new cases of cancer will be diagnosed in the United States per year (Varner, J., et al., Cell Adh. Commun. 1995; 3:367-374).

Metastasis, the spread of malignant tumor cells from the primary tumor mass to distant sites involves a complex series of interconnected events. (Liotta, et al., Cell 1991; 64:327-336; Wyckoff, et al., Cancer Res. 2000; 60:2504-2511; Kurschat, et al., Clinc. Exp. Dermatol. 2000; 25:482-489.) The metastatic cascade is initiated by a series of genetic alterations leading to changes in cell-cell interaction, which allow tumor cells to dissociate from the primary tumor mass. The dissociated cells locally invade and migrate through proteolytically modified extracellular matrix (ECM). The dissociated cells gain access to the circulatory system. To establish a metastatic deposit, the circulating tumor cells must evade host immune defenses, arrest in the microvasculature, and extravasate out of the circulation. The tumor cells then invade the ECM at the new site, proliferate, induce angiogenesis, and continue to grow.

Therapies designed to block angiogenesis may significantly effect the growth of solid tumors and metastases. Blocking tumor neovascularization significantly inhibits tumor growth in various animal models, and human clinical data is beginning to support this contention as well (Varner, J., et al., Cell Adh. Commun. 1995; 3:367-374). These and other studies suggest that the growth of solid tumors requires new blood vessel growth for continued expansion of the tumors beyond a minimal size (Varner et al., 1995; Blood, C. H., et. al., Biochim. Biophys. Acta. 1990; 1032:89-118; Weidner, N. et al. J Natl. Cancer Inst. 1992; 84:1875-1887; Weidner, N. et al., N. Engl. J Med. 1991; 324:1-7; Brooks, P. C. et al. J Clin. Invest. 1995; 96:1815-1822; Brooks, P. C. et al., Cell 1994; 79:1157-1164; Brooks, P. C. et al. Cell 1996; 85:683-693; Brooks, P. C. et al., Cell 1998; 92:391-400). Inhibition of angiogenesis is, therefore, a promising treatment for cancer and metastatic disease.

Angiogenesis is the physiological process by which new blood vessels develop from pre-existing vessels (Varner et al., 1995; Blood et al., 1990; Weidner et al., 1992). This complex process requires cooperation of a variety of molecules including growth factors, cell adhesion receptors, matrix degrading enzymes and extracellular matrix components (Varner et al., 1995; Blood et al., 1990; Weidner et al., 1992).

Inhibition of angiogenesis may also be useful in treating other diseases that are characterized by unregulated blood vessel development including, for example, ocular diseases (e.g., macular degeneration and diabetic retinopathy) and inflammatory diseases (e.g., arthritis and psoriasis) (Varner et al., 1995).

Many investigators have focused their anti-angiogenic approaches towards growth factors and cytokines that initiate angiogenesis (Varner et al., 1995; Blood et al., 1990; Weidner et al., 1992; Weidner et al., 1991; Brooks et al., 1995; Brooks et al., 1994; Brooks et al., 1997). There are, however, a large number of growth factors and cytokines that have the capacity to stimulate angiogenesis. The therapeutic benefit of blocking a single cytokine, therefore, may have only limited benefit due to this redundancy. Little attention has been directed to other anti-angiogenic targets.

Recent studies have suggested that angiogenesis requires proteolytic remodeling of the extracellular matrix (ECM) surrounding blood vessels in order to provide a microenvironment conducive to new blood vessel development (Varner et al., 1995; Blood et al., 1990; Weidner et al., 1992; Weidner et al., 1991; Brooks et al., 1995; Brooks et al., 1994; Brooks et al., 1997). Extracellular matrix proteins play more than just a structural role. They also display a diverse set of biological functions that regulate adhesion, migration, proliferation, differentiation and gene expression of adjacent cells (Roskelly, et al., Curr. Op. Cell Biol. 1995; 7:736-747).

Inhibition of angiogenesis would be a useful therapy for restricting tumor growth and metastases. Inhibition of angiogenesis may be effected by (1) inhibition of release of "angiogenic molecules" such as, for example, bFGF (basic fibroblast growth factor), (2) neutralization of angiogenic molecules, (e.g., anti-bFGF antibodies), and (3) inhibition of endothelial cell response to angiogenic stimuli. (Folkman et al., Cancer Biology. 1992; 3:89-96). Several potential endothelial cell response inhibitors have been described that might be used to inhibit angiogenesis, e.g., collagenase inhibitors, basement membrane turnover inhibitors, angiostatic steroids, fungal-derived angiogenesis inhibitors, platelet factor 4, thrombospondin, arthritis drugs such as D-penicillamine and gold thiomalate, vitamin D3 analogs, and alpha-interferon. Additional proposed inhibitors of angiogenesis have also been described in the literature (Blood, et al., 1990; Moses et al., Science. 1990; 248:1408-1410; Ingber, et al., Lab. Invest. 1988; 59:44-5 1; and U.S. Pat. Nos. 5,092,885; 5,112,946; 5,192,744; and 5,202,352.). Brooks, et al. (PCT WO 00/40597) discloses antibodies that bind to cryptic regions within various denatured collagen types.

Laminins are a large family of extracellular matrix glycoproteins. Laminins have been shown to promote cell adhesion, cell growth, cell migration, cell differentiation, neurite growth, and to influence the metastatic behavior of tumor cells (U.S. Pat. No. 5,092,885). Laminin, of which there are at least ten isoforms, is a major component of basement membranes and has been shown to mediate cell-matrix attachment, gene expression, tyrosine phosphorylation of cellular proteins, and branching morphogenesis (Streuli, et al., J. Cell Biol. 1993; 129:591-603; Malinda and Kleinman, Int. J. Biochem. Cell Biol. 1996; 28:957-1959; Timpl and Brown, Matrix Biol. 1994; 14:275-281; Tryggvason, Curr. Op. Cell Biol. 1993 5:877-882; Stahl, et al., J. Cell Sci. 1997; 110:55-63).

Laminin binds to type IV collagen, heparin, gangliosides, and cell surface receptors and promotes the adhesion and growth of various epithelial and tumor cells as well as neurite outgrowth. Laminin is thought to mediate cell-matrix interactions and to be a structural component of all basement membranes binding to collagen IV, heparin sulfate proteoglycan, and nidogen-entactin.

The laminin molecule is composed of three polypeptide chains (α, β, and γ) assembled into a cross-shaped structure. Different α, β, and γ chains may be combined, which accounts for the large size of the laminin family. (Jones, J. C. R. et al., Micr. Res. Tech. 2000; 51:211-213; Patarroyo, M. et al., Semin. Cancer Biol. 2002; 12:197-207). Denaturation of laminin may reveal cryptic regulatory regions that control angiogenesis, tumor growth and metastasis. Antagonism of these cryptic regions could provide an unrecognized means for the diagnosis and inhibition of angiogenesis, tumor growth and metastasis.

It has now been surprisingly discovered that antagonists selective for denatured laminin inhibit angiogenesis, tumor growth and metastasis. Peptide antagonists that specifically bind to denatured laminin provide the basis for powerful new compounds for treating cancer, inflammatory diseases and other angiogenesis-associated diseases.

SUMMARY OF THE INVENTION

Angiogenesis is necessary and important in the initiation, maintenance, growth and/or spread of cancer and other angiogenesis-associated diseases. The goal of inhibiting angiogenesis, and thereby treating cancer and these other diseases, is met by the selective antagonists of denatured laminin of the present invention. Moreover, the antagonists of the present invention directly inhibit adhesion of tumor cells to denatured laminin.

The invention provides a method for inhibiting angiogenesis, tumor growth and metastasis in the tissue of a mammal by administering to the mammal an active agent comprising an angiogenesis-inhibiting amount of a selective antagonist of denatured laminin.

The invention also provides a method for inhibiting tumor growth and metastasis in the tissue of a mammal by administering to the mammal an active agent comprising a tumor cell adhesion-inhibiting amount of a selective antagonist of denatured laminin.

The present invention also provides peptide antagonists that specifically bind to denatured laminin and can be used to inhibit angiogenesis, tumor growth and metastasis in mammals. More specifically, the invention provides biologically active agents comprising denatured laminin selective antagonists that inhibit angiogenesis, tumor growth and metastasis. The binding affinity of the peptide antagonists of the present invention to denatured laminin is substantially greater than the binding affinity of the antagonists to native forms of laminin.

A preferred denatured laminin selective antagonist for use in the present invention is a peptide having the amino acid sequence $NH_2$-S-T-Q-N-A-S-L-L-S-L-T-V-C-COOH (SEQ ID NO 1).

Another preferred denatured laminin selective antagonist for use in the present invention is a peptide having the amino acid sequence $NH_2$-K-G-G-C-S-T-Q-N-A-Q-L-L-S-L-I-V-G-K-A-COOH (STQ-peptide) (SEQ ID NO 2).

Another preferred denatured laminin selective antagonist for use in the present invention is a peptide having the amino acid sequence $NH_2$-K-G-G-S-T-Q-N-A-Q-L-L-S-L-J-V-G-K-A-COOH (STQ-peptide-S) (SEQ ID NO 3).

In another embodiment of the invention, the denatured laminin selective antagonist is conjugated to a cytotoxic or cytostatic agent.

In another aspect, the invention provides methods for detecting angiogenesis in a mammalian tissue by exposing the tissue to a detectably labeled denatured laminin selective antagonist.

In a still further embodiment, the invention includes a method for detecting tumorous tissue, metastases, tumor invasion, bacterial invasion, arthritis, inflammation or any other disease or condition that is characterized or associated with denaturation of laminin in a mammalian tissue by exposing the tissue to be tested to a detectably labeled denatured laminin selective antagonist.

DETAILED DESCRIPTION OF THE INVENTION

Figure 1:
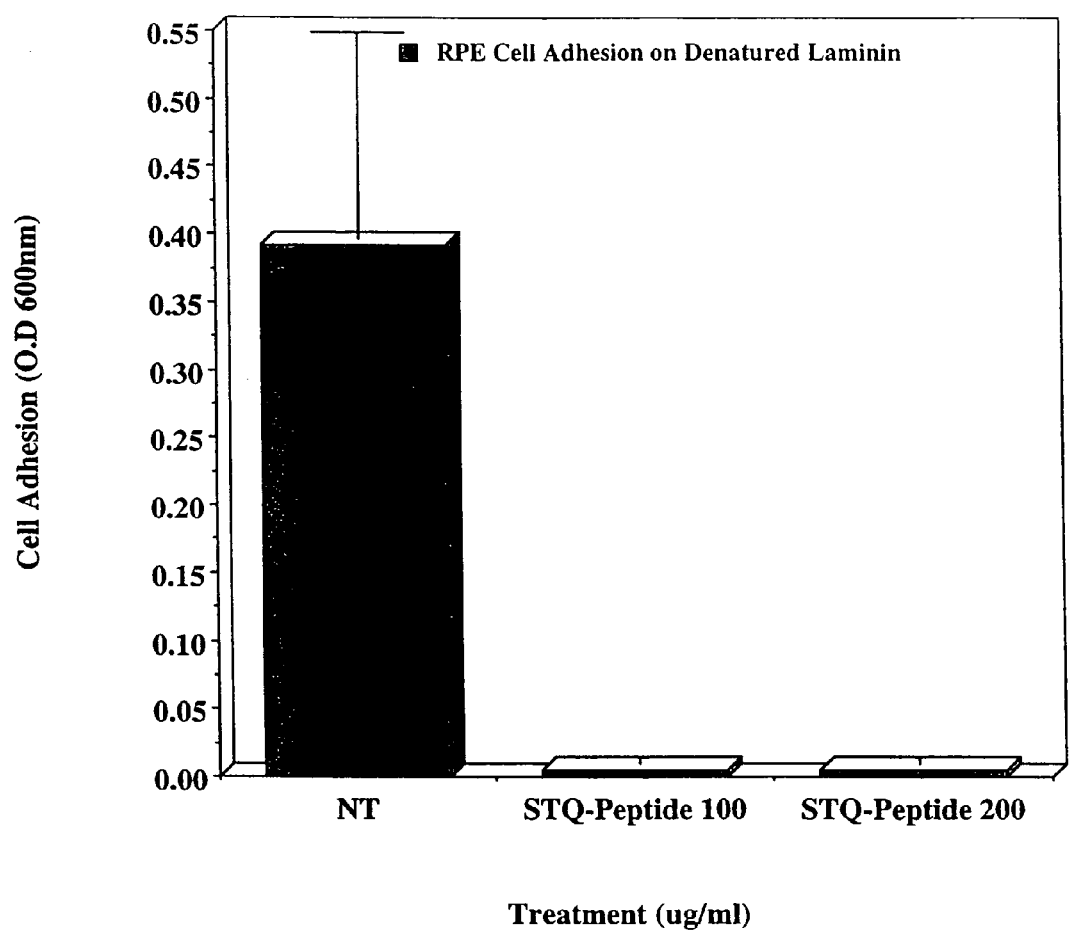
FIG. 1 is a chart which illustrates human retinal pigmented epithelial (RPE) cell adhesion to untreated denatured laminin (NT), STQ-peptide treated denatured laminin at a STQ-peptide concentration of 100 μg/ml, and STQ-peptide treated denatured laminin at a STQ-peptide concentration of 200 μg/ml.

The present invention provides compositions and methods for inhibiting angiogenesis, tumor growth, metastasis, bacterial invasion, arthritis, inflammation or any other disease or condition that is characterized or associated with denaturation of laminin in mammals and for detecting angiogenesis, tumor growth, metastasis, bacterial invasion, arthritis, inflammation or any other disease or condition that is characterized or associated with denaturation of laminin in mammalian tissue through the use of denatured laminin selective antagonists.

The methods of the present invention provide biologically active agents that inhibit the formation of new blood vessels required to establish and sustain cancer cells. Additionally, the present invention provides methods and compositions that directly inhibit tumor growth, metastasis, inflammation, and other diseases or conditions associated with cellular interactions with denatured laminin. The active agents of the present invention selectively bind to denatured laminin thereby preventing angiogenesis, tumor growth, metastasis, arthritis, inflammatory diseases and other diseases or conditions associated with cellular interactions with such laminin.

Definitions

As used herein, the term "angiogenesis" includes a variety of processes involving neovascularization of a tissue including "sprouting", vasculogenesis, or vessel enlargement. All of these angiogenesis processes involve disruption of the extracellular matrix protein laminin within the basement membrane of blood vessels. Angiogenesis that takes place during traumatic wound healing, corpus luteum formation and embryogenesis is a part of normal physiology. The majority of mammalian angiogenesis conditions, however, are associated with disease processes.

As used herein, "antagonist" refers to a compound that inhibits a naturally occurring biological activity.

As used herein, a "cryptic epitope" is a laminin sequence that is not exposed for recognition within a native laminin, but is capable of being recognized by an antagonist of a denatured laminin. Peptide sequences that are not solvent exposed, or are only partially solvent exposed, in the native structure are potential cryptic epitopes. If an epitope is not solvent exposed, or only partially solvent exposed, then it is likely that it is buried within the interior of the molecule. The sequence of cryptic epitopes can be identified by determining the specificity of an antagonist. Candidate cryptic epitopes also can be identified, for example, by examining the three dimensional structure of a native laminin.

As used herein "laminin" refers to a family of extracellular matrix proteins composed of an α, β, and γ chain. (Jones, J. C. R. et al., Micr. Res. Tech. 2000; 51:211-213; Patarroyo, M. et al., Semin. Cancer Biol. 2002; 12:197-207).

As used herein "native laminin" refers to laminin that is predominately in its naturally occurring native form.

As used herein "denatured laminin" refers to laminin that is no longer predominantly in its naturally occurring native form. The denatured laminin can be denatured full-length laminin or a fragment of laminin. A fragment of laminin can be any laminin sequence shorter than a full length laminin sequence. For fragments of laminin with substantial native structure, denaturation can be effected as for a native full-length laminin. Fragments also can be of a size such that they do not possess significant native structure or possess regions without significant native form. The term "denatured laminin" encompasses "proteolyzed laminin". "Proteolyzed laminin" refers to a laminin that has been structurally altered through the action of a proteolytic enzyme.

As used herein, a "denatured laminin selective antagonist" is a substance that has a substantially greater binding affinity to denatured laminin than to native laminin.

As used herein, an "epitope" is that amino acid sequence or sequences that are recognized by an antagonist of the invention. An epitope can be a linear peptide sequence or can be composed of noncontiguous amino acid sequences. An antagonist can recognize one or more sequences, therefore an epitope can define more than one distinct amino acid sequence target. The epitopes recognized by an antagonist can be determined by peptide mapping and sequence analysis techniques well known to one of skill in the art.

The term "peptide" as used herein refers to a series of two or more covalently linked amino acids. A linear, cyclic, or branched peptide can be used in practicing the invention.

As used herein, the term "peptido-mimetic" is used to refer to compounds that mimic the activity of a peptide. Peptido-mimetics are non-peptides but may comprise amino acids linked by non-peptide bonds. In a peptido-mimetic, the three dimensional structure of a peptide that specifically interacts with the three dimensional structure of a cryptic epitope is duplicated by a molecule that is not a peptide.

"Neovascularization" as used herein means the development of new blood vessels. Neovascularization may refer to the process of angiogenesis and/or to the result of angiogenesis, which is new blood vessel formation.

As defined herein, a "patient" is any mammal in which treatment of angiogenic diseases, tumor growth or metastasis is desirable. Preferred patients include agricultural or domestic mammals; for example, a pig, a cow, a horse, a goat, a sheep, a mule, a donkey, a dog, a cat, a rabbit, a mouse, and a rat. An especially preferred patient is a human.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Substantially greater affinity" means a binding affinity at least 1.5-fold greater for the target compound as compared to the standard compound and, more preferably, at least 10-fold greater and, most preferably, at least 100-fold greater. The selective antagonists are specific for denatured laminin (the target compound) and the binding affinities of the selective antagonists are compared to native laminin (the standard compound). Apparent binding affinity measurements can be made using enzyme linked immunosorbent assay (ELISA) or other techniques familiar to one of skill in the art, e.g., surface plasmon resonance technique (analyzed on a BIOCORE 2000 system) (Liljeblad, et al., Glyco. J. 2000; 17: 323-329), and standard measurements and traditional binding assays (Heeley, R. P., Endocr. Res. 2002; 28: 217-229).

A "therapeutically effective amount" is an amount of denatured laminin selective antagonist sufficient to produce a measurable decrease in angiogenesis in the tissue being treated, i.e., an angiogenesis-inhibiting amount; or an amount of denatured laminin selective antagonist sufficient to produce a measurable decrease in tumor growth, metastasis, arthritis, inflammatory disease or condition associated with denatured laminin.

The term "treatment" is used herein to mean the administration of a denatured laminin selective antagonist to prevent angiogenesis, tumor growth, metastasis, bacterial invasion, arthritis, inflammation or any other disease or condition that is characterized or associated with denaturation of laminin or to inhibit the progression of pre-existing angiogenesis, tumor growth, metastasis, bacterial invasion, arthritis, inflammation or any other disease or condition that is characterized or associated with denaturation of laminin in a patient with such a disease or condition, and/or to ameliorate symptoms associated with such diseases or conditions.

The term "unit dose" when used in reference to a therapeutic composition of the present invention refers to a physically discrete unit suitable as a unitary dosage for the subject, each unit containing a predetermined quantity of active material calculated to produce the desired therapeutic effect either alone or in a composition comprising a suitable diluent; carrier, vehicle, or other excipient.

Denatured Laminin Antagonists

The biologically active agents of the present invention comprise compounds that have a strong binding affinity for denatured laminin. A denatured laminin selective antagonist of the present invention contains amino acid sequences that bind with substantially greater affinity to denatured laminin than to native laminin.

One preferred denatured laminin selective antagonist for use in the present invention is STQ-peptide. STQ-peptide binds to denatured laminin with high specificity. The amino acid sequence of STQ peptide is NH$_2$-K-G-G-C-S-T-Q-N-A-Q-L-L-S-L-I-V-G-K-A-COOH (SEQ ID NO 2). The STQ-peptide binds to regions within denatured laminin and inhibits cellular interactions with denatured laminin. Adhesive cellular interactions with functional epitopes within the extracellular matrix have a role in regulating angiogenesis, tumor growth and metastasis in vivo. (Xu, J., et al., J. Cell Biol. 2001; 154:1069-1079; Hangia, et al., Am. J. Pathol. 2002; 161:1429-1437). STQ-peptide has been shown to potently block angiogenesis (Example 5 below) and tumor growth and metastasis (Example 6 below) in vivo.

Another preferred denatured laminin selective antagonist for use in the present invention is STQ-peptide-S. STQ-peptide-S binds with high specificity to denatured laminin and inhibits cellular interactions with denatured laminin. The amino acid sequence of STQ-peptide-S is NH$_2$-K-G-G-S-T-Q-N-A-Q-L-L-S-L-I-V-G-K-A-COOH (SEQ ID NO 3).

A further preferred denatured laminin selective antagonist for use in the present invention has the amino acid sequence NH$_2$-S-T-Q-N-A-S-L-L-S-L-T-V-C-COOH (SEQ ID NO 1), which binds with high specificity to denatured laminin and inhibits cellular interactions with denatured laminin.

Sequential solid phase binding assays, for example, can be used to identify denatured laminin selective antagonists. Preferred methods for identifying denatured laminin antagonists are subtractive immunization (Xu, J. et al., Hybridoma. 2000; 19:375-385) and subtractive phage display (Amstutz P., et al., Curr. Opin. Biotechnol. 2001; 12:400-405).

A preferred method of denaturation is thermal denaturation because thermal denaturation results in fewer small fragments that may have little immunogenicity in vivo. Laminin can be thermally denatured by, for example, heating laminin to 100° C. for fifteen minutes. Denaturation can also be accomplished by treating the laminin with a chaotropic agent. Suitable chaotropic agents include, for example, guanidinium salts. Laminin can also be denatured by ionizing radiation, non-ionizing radiation (ultraviolet), thermal injury, and mechanical stress or force. Laminin can also be denatured by proteolysis. In particular, proteolyzed laminin can be prepared by treating the laminin with a metalloproteinase (e.g., MMP-1, MMP-2 or MMP-9), elastase or by treating the laminin with a cellular extract containing laminin degrading activity. Proteolyzed laminin may also occur naturally at sites of neovascularization, tumor growth, metastasis, bacterial invasion, arthritis and inflammation in a tissue.

Denaturation of a laminin can be monitored, for example, by spectroscopic changes in optical properties such as absorbance, circular dichroism or fluorescence of the protein, by nuclear magnetic resonance, by Raman spectroscopy, or by any other suitable technique.

The resultant denatured laminin fragments can then be fixed to a solid matrix. Peptides known to bind laminin can be obtained from a peptide library. (Amstutz P., et al., Curr. Opin. Biotechnol. 2001; 12:400-405). The laminin-binding peptides can be passed over the solid matrix. Peptides that bind denatured laminin adhere to the solid matrix. The adherent peptides can then be washed from the solid matrix and then passed over a second solid matrix to which native laminin is fixed. Peptides that do not bind to the second solid matrix are denatured laminin selective antagonists.

The selective peptide and polypeptide antagonists used in the present invention can be generated using several different techniques that are well known to those skilled in the art. For example, a two hybrid system (e.g., Fields, S., Nature. 1989; 340:245-6) uses a laminin fragment as "bait" for selecting protein antagonists from a library that binds to the laminin peptide. This system and its operation are described in Green, D. M., et al., Proc. Natl. Acad. Sci. USA. 2003; 100:1010-1015 and in Gyuris, J. et al., Cell. 1993 75: 791-803. The library of potential antagonists can be derived from a cDNA library, for example. In another embodiment, the potential antagonists can be variants of known laminin binding proteins such as integrins α6β4 and α3β1, collagen and certain proteoglycans (Belkinb, A. M., Stepp, M. A., Micro. Res. Tech. 2000; 51:280-301; Jones, J. C. R. et al., Micr. Res. Tech. 2000; 51:211-213; Patarroyo, M. et al., Semin. Cancer Biol. 2002; 12:197-207). Such proteins can be randomly mutagenized or subjected to gene shuffling, or other well known techniques for generating sequence diversity. (Tani, P. H., et al., Biochm. J. 2002; 365:287-294; Stephanopoulos, G., Nat. Biotechnol., 2002; 20:666-668)

Peptide antagonists of the invention also can be generated using molecular evolution techniques as disclosed in Zhao, H., et al., Cur. Opin. Biotechnol. 2002; 13:104-110 and Guo, Z., et al., Biochemistry. 2002; 41:10603-10607. Libraries of proteins can be generated by mutagenesis, gene shuffling or other well known techniques for generating molecular diversity. Protein pools representing numerous variants can be selected for their ability to bind to denatured laminin, for instance, by passing such protein pools over a solid matrix to which a denatured laminin has been attached. Elution with gradients of salt, for example, can provide purification of variants with affinity for the denatured laminin. A negative selection step also can be included whereby such pools are passed over a solid matrix to which native laminins have been attached. The filtrate will contain those variants with in the pool that have a reduced affinity for the native form of the laminin.

The peptide and polypeptide antagonists of the present invention also can be generated by phage display. Phage display is a selection technique in which a peptide is expressed as a fusion with a coat protein of a bacteriophage. The result is that the fused protein is displayed on the surface of the viron and the DNA encoding the fusion protein resides within the viron. (Smith G. P., Science 1985; 228:1315-1317; Smith G. P., et al., Methods Enzymol. 1993; 217:228-257) Phage display allows for rapid identification of peptide ligands for a variety of target molecules using an in vitro process called panning. Panning is carried out, for example, by incubating a library of phage-displayed peptides with a microtiter plate coated with the target, washing away the unbound phage, and eluting the bound phage. The eluted phage is then amplified and taken through additional binding/amplification cycles to enrich the pool in favor of binding sequences. After 3-4 rounds of panning, individual clones are identified by DNA sequencing.

A randomized peptide or protein can be expressed on the surface of a phagemid (a term for the combination of phage and plasmid) particle as a fusion with a phage coat protein. Techniques of monovalent phage display are widely available (see, e.g., Lowman H. B. et al., Biochemistry. 1991; 30:10832-8.) Phage expressing randomized peptide or protein libraries can be panned with a solid matrix to which a native laminin molecule has been attached. Remaining phage do not bind native laminins, or bind native laminins with substantially reduced affinity. The phage are then panned against a solid matrix to which a denatured laminin has been attached. Bound phage are isolated and separated from the solid matrix by either a change in solution conditions or, for a suitably designed construct, by proteolytic cleavage of a linker region connecting the phage coat protein with the randomized peptide or protein library. The isolated phage can be sequenced to determine the identity of the selected antagonist.

The well known ELISA assay can be used to identify laminin selective antagonists for use in practicing the present invention.

A peptide or polypeptide can be identified as an antagonist through the use of a solid phase ELISA to determine whether the peptide or polypeptide binds to denatured or native laminins. The ELISA assay is useful with a variety of laminin types, as well as for other extracellular matrix components. The level of binding affinity can be determined by surface plasmon resonance technique (analyzed on a BIOCORE 2000 system) (Liljeblad, et al., Glyco. J. 2000; 17:323-329) and standard measurements by traditional scatchard binding assays (Heeley, R. P., Endocr. Res. 2002; 28:217-229).

Solid phase ELISA also can be used to identify compounds which exhibit specificity for denatured, but not native, forms of laminin. The specificity assay is conducted by running parallel ELISAs where a potential antagonist is screened concurrently in separate assay chambers for the ability to bind denatured and native laminins.

Antagonists can also be identified by their ability to bind to a solid matrix containing a denatured laminin. Putative antagonists are collected after altering solution conditions, such as salt concentration, pH, temperature, etc. The putative antagonists are further identified by their ability to pass through, under appropriate solution conditions, a solid matrix to which a native laminin has been affixed.

The antagonists of the present invention can be used with laminin molecules from any invertebrate or vertebrate animal, including humans. Examples of laminin molecules are found in Belkinb, A. M., Stepp, M. A., Micro. Res. Tech. 2000; 51:280-301; Jones, J. C. R. et al., Micr. Res. Tech. 2000; 51:211-213; and Patarroyo, M. et al., Semin. Cancer Biol. 2002; 12:197-207. Preferably, the laminin is a mammalian laminin. More preferably, the mammal is a pig, cow, goat, rabbit, mouse, rat, dog, cat, sheep, donkey, horse, or mule. In a particularly preferred embodiment, the laminin is human laminin.

The active agents for use in the invention comprise one or more denatured laminin antagonists. An antagonist of denatured laminin can be any peptide, polypeptide or peptidomimetic (such as an organic compound, a carbohydrate or a chemical) that has substantially greater binding affinity to denatured laminin than to the native form of laminin.

The peptide antagonists of the present invention may be modified, for example, by phosphorylation, hydroxylation or methylation. Additional modifications that may enhance activity include peptide cyclization and peptide stabilization.

In another embodiment; the present invention includes analogs, fragments, or chemical derivatives of a polypeptide whose amino acid residue sequence is shown herein so long as the peptide is an antagonist of denatured laminin, but not of native laminin. Therefore, a peptide can be subject to various changes, substitutions, insertions, and deletions where such changes provide for certain advantages in its use. In this regard, a denatured laminin antagonist peptide of this invention includes the sequence of a recited peptide where one or more sequence changes are made and the peptide retains the ability to function as a denatured laminin selective antagonist in one or more of the assays as defined herein.

The coupling of the amino acids may be accomplished by techniques familiar to those in the art and provided, for example, in Stewart and Young, Solid Phase Synthesis, 1984, Second Edition, Pierce Chemical Co., Rockford, Ill.

The antagonist can be conjugated with cytotoxins such as cisplatin, vinblastine and gemcitabine, for delivery to a tumor or other tissue undergoing angiogenesis, tumor growth, metastasis, arthritis or other disease or condition associated with cellular interactions with denatured laminin. Such conjugates can be made with a cytolysin or an exotoxin, for example ricin A, diphtheria toxin A, or *Pseudomonas* exotoxin and fragments thereof. A preferred cytotoxin for use in the present invention is cisplatin. The cytotoxic agent can also be a radioactively labeled with an isotope so as to locally deliver a toxic dose of radioactivity to an angiogenic tissue, tumor growth, metastasis or other tissue undergoing cellular interaction with denatured laminin.

The antagonist can be conjugated with a cytostatic agent such as an anti-angiogenic compound, for delivery to a tumor or other tissue undergoing angiogenesis, tumor growth, metastasis, arthritis or other disease or condition associated with cellular interactions with denatured laminin. A preferred cytostatic agent is a matrix metalloproteinase (MMP) inhibitor. A preferred MMP inhibitor is Marimistat (available from British Biotech, Oxford, United Kingdom).

In Vivo Assays for Angiogenesis Inhibition

The selective peptide antagonists of the present invention can be assayed for their ability to modulate angiogenesis in a tissue. Any suitable assay known to one of skill in the art, such as the chick chorioallantoic membrane (CAM) assay, or the rabbit eye assay, or the chimeric mouse assay can be used to monitor such effects. Several non-limiting techniques are described herein.

One angiogenesis assay measures angiogenesis in the chick chorioallantoic membrane (CAM) and is referred to as the CAM assay. The CAM assay is well known among those of ordinary skill in the art and has been used to measure both angiogenesis and neovascularization of tumor tissues (Ausprunk et al., Am. J. Pathol. 1975; 79:597-618 and Ossonski et al., Cancer Res. 1980; 40:2300-2309).

During the CAM assay, angiogenesis of whole tissue is occurring. The assay measures growth of chick embryo blood vessels into the CAM or into the tissue grown on the CAM. Accordingly, the CAM assay is a valid model for in vivo angiogenesis.

The CAM assay measures inhibition of angiogenesis based on both the amount and extent of new vessel growth. It is furthermore possible to monitor the growth of any tissue transplanted upon the CAM, such as a tumor tissue.

Finally, the CAM assay is particularly useful because there is an internal control for toxicity in the assay system. During the assay a viable, developing chick embryo is exposed to test reagent. The health of the embryo is an indication of toxicity.

In another assay, angiogenesis is measured in an in vivo rabbit eye model, referred to as the "rabbit eye assay". The rabbit eye assay is well known among those of ordinary skill in the art and has been used to measure both angiogenesis and neovascularization in the presence of angiogenic inhibitors such as thalidomide. (D'Amato et al., Proc. Natl. Acad. Sci. 1994; 91:4082-4085).

The rabbit eye assay is a well recognized assay model for in vivo angiogenesis because angiogenesis, exemplified by rabbit blood vessels growing from the rim of the cornea into the cornea, is easily visualized through the naturally transparent cornea of the eye. Additionally, both the extent and the amount of stimulation or inhibition of angiogenesis, or regression of angiogenesis, can easily be monitored over time.

The rabbit is exposed to any test reagent used, and therefore the health of the rabbit is an indication of toxicity of the test reagent.

Another assay measures angiogenesis in a chimeric mouse:human model and is referred to as the chimeric mouse assay. (Yan, et al., J Clin. Invest. 1993; 91:986-996). The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers.

The chimeric mouse assay demonstrates regression of neovascularization based on both the amount and extent of regression of new vessel growth. Furthermore, effects on the growth of any tissue transplanted upon the grafted skin, such as a tumor tissue, may be monitored. Finally, the assay is useful because there is an internal control for toxicity in the assay system. The chimeric mouse is exposed to any test reagent used, and therefore the health of the mouse is an indication of toxicity.

Disease Treatment

It has now been discovered that binding of certain epitopes of denatured laminin, but not of native laminin, to selective antagonists inhibits angiogenesis, tumor growth, metastasis, arthritis, and other conditions or diseases associated with cellular interactions with denatured laminin in the tissues of mammals, including humans and other animals. Angiogenesis is required in a variety of disease processes. By inhibiting angiogenesis, one can intervene in the disease, ameliorate the symptoms and, in some cases, cure the disease.

Where the growth of new blood vessels is required to support growth of abnormal tissue, inhibition of angiogenesis will reduce the blood supply to the tissue and thereby contribute to reduction in tissue mass based on blood supply requirements. Examples include growth of tumors, where neovascularization is a continual requirement in order that the tumor grow beyond a few millimeters in thickness, and for the establishment of solid tumor metastases. Where the growth of new blood vessels is the cause of, or contributes to, the pathology associated with a disease, inhibition of angiogenesis will reduce the deleterious effects of the disease. Examples include psoriasis, rheumatoid arthritis, diabetic retinopathy, inflammatory diseases, restenosis, macular degeneration and the like.

The methods of the present invention are effective in part because the therapy is highly selective for angiogenesis and other processes involving cellular interaction with denatured laminin, and not other biological processes. The discovery that binding of denatured laminins alone can effectively inhibit angiogenesis and other processes involving cellular interaction with denatured laminin allows for the development of therapeutic compositions with potentially high specificity, and therefore relatively low toxicity.

The present method for inhibiting angiogenesis in a tissue and, therefore, for practicing the methods for treatment of angiogenesis-related diseases, comprises administering to a patient in need of angiogenic treatment a composition comprising a therapeutically effective amount of a denatured laminin selective antagonist capable of binding selectively to denatured or proteolyzed laminin, compared to binding native laminin. Thus, the method comprises administering to a patient a therapeutically effective amount of a pharmaceutical composition comprising a denatured laminin selective antagonist of the invention.

The invention provides a method for inhibiting angiogenesis, tumor growth, metastasis, arthritis, inflammatory diseases and other diseases or conditions associated with cellular interactions with denatured laminin in the tissue of an animal in need of such treatment, including mammals and humans, and, thereby, inhibiting events in the tissue which depend upon angiogenesis. Generally, the method comprises administering to an animal a composition comprising an effective angiogenesis-inhibiting amount of a denatured laminin selective antagonist.

The present invention also provides a method for inhibiting tumor neovascularization by inhibiting tumor angiogenesis. In certain embodiments, the tissue to be treated is a tumor tissue of a patient with a solid (malignant) tumor, a metastases, a skin cancer, a breast cancer, a hemangioma or angiofibroma and the like cancer; and the angiogenesis to be inhibited is tumor tissue angiogenesis where there is neovascularization of a tumor tissue. Typical solid tumor tissues treatable by the present methods include lung, pancreas, breast, colon, laryngeal, ovarian, Kaposi's sarcoma and similar tissues.

Inhibition of tumor tissue angiogenesis is a significant development because of the important role neovascularization plays in tumor growth. In the absence of neovascularization, tumor tissue does not obtain the required nutrients, slows in growth, ceases additional growth, regresses and ultimately becomes necrotic resulting in killing or eliminating the tumor. An additional significant development is the direct inhibition of tumor growth and metastasis by blocking tumor cell adherence to denatured laminin and, thereby, preventing the tumor cell from becoming established in the tissue.

In another aspect, the invention provides methods for inhibiting tumor growth and the formation of metastases through administration of biologically active compositions comprising antagonists of denatured laminin. These methods are particularly effective because (1) formation of metastases requires denaturation of laminin and vascularization of a primary tumor so that the metastatic cancer cells can exit the primary tumor and (2) establishment of a tumor in a secondary site requires denaturation of laminin and neovascularization to support growth of the metastases.

Additionally, the invention provides methods for inhibiting tumor growth and metastasis by directly inhibiting tumor cell interaction with denatured laminin. A tumor cell must adhere to a tissue in order to establish itself in the tissue and, subsequently, grow. The methods and compositions of the present invention directly inhibit tumor cell adherence to tissue by blocking tumor cell interaction with denatured laminin.

In further embodiments, the invention enables any of the foregoing methods to be carried out in combination with other therapies such as, for example, chemotherapy directed against solid tumors. An angiogenesis inhibitor may be administered to a patient in need of such treatment before, during, or after chemotherapy. Preferably an angiogenesis inhibitor is administered to a patient after a regimen of chemotherapy. At such time, the tumor tissue responds to the toxic assault by inducing angiogenesis in order to recover by the provision of blood and nutrients to the tumor tissue. It is also preferred to administer an angiogenesis inhibitor to a patient as a prophylaxis against metastases after surgery on the patient for the removal of solid tumors.

Accordingly, the methods of inhibiting tumor growth, metastasis, and neovascularization disclosed in this application can be applied to inhibit tumor tissue growth, to inhibit tumor metastases formation, and to cause regression of established tumors.

There are a variety of diseases in which angiogenesis is believed to be important. These are referred to as angiogenic diseases, including but not limited to, inflammatory disorders such as immune and non-immune inflammation, chronic articular rheumatism and psoriasis; disorders associated with inappropriate or inopportune invasion of vessels such as diabetic retinopathy, neovascular glaucoma, restenosis, capillary proliferation in atherosclerotic plaques and osteoporosis; and cancer associated disorders, such as solid tumors, solid tumor metastases, angiofibromas, retrolental fibroplasia, hemangiomas, Kaposi's sarcoma and the like cancers which require neovascularization to support tumor growth. Other suitable tumors include melanoma, carcinoma, sarcoma, fibrosarcoma, glioma and astrocytoma.

Thus, methods which inhibit angiogenesis in a diseased tissue treat and ameliorate symptoms of the disease and, depending upon the disease, can contribute to a cure.

In one embodiment, the present invention contemplates a method for inhibition of angiogenesis in a mammalian, e.g. human, tissue by administration of a denatured laminin selective antagonist.

As described herein, any of a variety of tissues, or organs comprised of organized tissues, can support angiogenesis in disease conditions including skin, muscle, gut, connective tissue, joints, bones and the like tissue, in which blood vessels can invade upon angiogenic stimuli. Tissue, as used herein, encompasses all bodily fluids, secretions and the like, such as, for example, serum, blood, cerebrospinal fluid, plasma, urine, synovial fluid, vitreous humor.

Thus, in one related embodiment, the tissue to be treated is an inflamed tissue and the angiogenesis to be inhibited is inflamed tissue angiogenesis where there is neovascularization of inflamed tissue. In this class, the method contemplates inhibition of angiogenesis in arthritic tissues (e.g., such as in a patient with chronic articular rheumatism), in immune or non-immune inflamed tissues, (e.g., in psoriatic tissue).

In another embodiment, the tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

Restenosis is a process of smooth muscle cell (SMC) migration and proliferation at the site of previous stenosis in a blood vessel. The migration and proliferation of SMCs associated with blood vessels during restenosis is related to the process of angiogenesis which is inhibited by the present methods and compositions. The invention also contemplates inhibition of restenosis by inhibiting angiogenic related processes according to the present methods and compositions in a patient following a procedure to correct vascular stenosis. Accordingly, the methods and compositions disclosed herein can be used at sites of percutaneous transluminal coronary angioplasty, coronary artery bypass, peripheral artery bypass, mesenteric artery bypass, and carotid endarterectomy or angioplasty.

The dose ranges for the administration of the denatured laminin selective antagonist depend upon the form of the antagonist and its potency, and are amounts large enough to produce the desired effect in which angiogenesis and the disease symptoms mediated by angiogenesis are ameliorated. The dosage should not be so large as to cause adverse side effects such as hyperviscosity syndromes, pulmonary edema, congestive heart failure, and the like. Generally, the dose will vary with the age, condition, sex and extent of the disease in the patient and can be determined by one of skill in the art. The dose also can be adjusted by the physician in the event of any complication.

Potency of a denatured laminin selective antagonist can be measured by a variety of means including, for example, inhibition of angiogenesis in the CAM assay, in the in vivo rabbit eye assay, in the in vivo chimeric mouse:human assay as discussed herein.

A therapeutically effective amount of a denatured laminin antagonist of this invention is typically an amount of peptide such that when administered in a pharmaceutically acceptable composition is sufficient to achieve a plasma concentration of from about 0.1 microgram (µg) per milliliter (ml) to about 200 µg/ml, preferably from about 1 µg/ml to about 150 µg/ml. Based on a polypeptide having a mass of about 500 grams per mole, the preferred plasma concentration in molarity is from about 2 micromolar (EM) to about 5 millimolar (mM) and preferably about 100 µM to 1 mM polypeptide antagonist. Stated differently, the dose per body weight can vary from about 0.1 mg/kg to about 300 mg/kg, and preferably from about 0.2 mg/kg to about 200 mg/kg, in one or more dose administrations daily, for one or several days.

Denatured laminin selective antagonists can be administered, for example, parenterally, by injection, or by gradual infusion over time. A preferred mode of administration for preventing angiogenesis is by intravenous administration of therapeutic compositions containing one or more of the biologically active agents of the present invention. Thus, antagonists and derivatives thereof can be administered intravenously, intraperitoneally, intramuscularly, subcutaneously, intracavity, transdermally, topically, intraocularly, orally, intranasally and can be delivered by peristaltic means. The therapeutic compositions of this invention may be administered intravenously, as by injection of a unit dose, for example In a preferred embodiment, the denatured laminin selective antagonist is administered in a single intravenous dose.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgment of the physician and are peculiar to each individual. However, suitable dose ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Inhibition of angiogenesis and tumor regression may occur as early as 7 days after the initial administration of the antagonist. Preferably, administration of antagonist is repeated resulting in tissue exposure to the antagonist for between 7 days and 6 weeks, more preferably between about 14 and 28 days.

For inhibition of restenosis, the denatured laminin selective antagonist is typically administered after the stenosis-relieving procedure for from about 2 to about 28 days, and more typically for about the first 14 days following the procedure.

Therapeutic Compositions

The present invention contemplates therapeutic compositions useful for practicing the therapeutic methods of the present invention. Therapeutic compositions of the present invention contain a pharmaceutically acceptable carrier together with a denatured laminin selective antagonist as described herein, dissolved or dispersed therein as an active ingredient. In a preferred embodiment, the therapeutic denatured laminin selective antagonist composition is not immunogenic when administered to a mammal or human patient for therapeutic purposes. A preferred denatured laminin selective antagonist is STQ-peptide. Another preferred denatured laminin selective antagonist is STQ-peptide-S. Another preferred denatured laminin selective antagonist has the amino acid sequence $NH_2$-S-T-Q-N-A-S-L-L-S-L-T-V-C-COOH (SEQ ID NO 1).

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use also can be prepared. The preparation also can be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, 3 ammonium, calcium or ferric hydroxides, and such organic bases as isopropylamine, trimethylamine, 2-ethylamino ethanol, histidine, procaine and the like. Particularly preferred are the salts of TFA and HCl.

Pharmaceutically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting, tumor growth-inhibiting, or metastasis-inhibiting amount of a denatured laminin selective antagonist of the present invention, formulated to contain 0.01 to 90 weight percent of antagonist per weight of total therapeutic composition. A preferred therapeutic composition formulation contains 0.05 to 50 weight percent of antagonist per weight of total therapeutic composition. A most preferred therapeutic composition formulation contains 0.1 to 20 weight percent of antagonist per weight of total therapeutic composition. A weight percent is a ratio by weight of inhibitor to total therapeutic composition. Thus, for example, 0.1 weight percent is 0.1 grams of inhibitor per 100 grams of total composition.

Detection Methods

Denatured laminin antagonists of the invention also are suitable for detection of angiogenesis, tumor growth, arthritis or other diseases or conditions associated with cellular interaction with denatured laminin in tissues. Such methods of detection may be used ex vivo and in vivo. An ex vivo method, for example, is the detection of angiogenesis, tumor growth or metastasis in a biopsy specimen.

Binding of detectably labeled denatured laminin selective antagonists to target tissue can be detected either directly or indirectly. Direct detection can be preformed on said antagonists comprising a detectable label such as a fluorochrome, a radioactive tag, paramagnetic heavy metal or diagnostic dye.

Indirect detection is performed using a detectable secondary reagent that interacts with the denatured laminin selective antagonist. A detectably labeled antibody that recognizes said antagonist can be used, for example, to visualize the location of the antagonist. Other methods of indirect detection are also known to those of ordinary skill in the art.

In vivo imaging methods permit the detection of a labeled antagonist that specifically binds to denatured laminin in the subject's body. The labeled antagonist is administered to a patient e.g., intravenously or intramuscularly. In vivo detection methods include magnetic resonance spectroscopy, positron-emission tomography (PET) and single photon emission tomography (SPECT). For purposes of in vivo imaging, the type of detection instrument available is a major factor in selecting a given label. For instance, radioactive isotopes and paramagnetic isotopes are particularly suitable for in vivo imaging. The type of instrument used will guide the selection of the radionuclide. For instance, the radionuclide chosen must have a type of decay which is detectable for a given type of instrument. However, any conventional method for visualizing diagnostic imaging can be utilized in accordance with this invention. In one embodiment, a radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA). Examples of metallic ions suitable as radioactive isotopes are $^{99}mTc$, $^{123}I$, $^{131}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}$Tl. Examples of paramagnetic isotopes, particularly useful in Magnetic Resonance Imaging (MRI), include $^{157}$Gd, $^{55}$Mn, $^{162}$Dy, $^{52}$Cr, and $^{56}$Fe.

EXAMPLES

The following Examples illustrate the invention, but are not limiting.

Example 1

Generation of Peptides that Specifically Bind to Denatured Laminin Epitopes

Subtractive phage display was used to generate peptides that specifically bind to denatured laminin. Peptides were expressed as a fusion with a coat protein of a bacteriophage on the surface of a viron. Panning was carried out by incubating a library of phage-displayed peptides with a microtiter plate coated with the target (native laminin in wells 1-4, denatured laminin in well 5), washing away the unbound phage, and eluting the specifically-bound phage. The eluted phage was amplified and taken through repeated panning to enrich the pool in favor of binding sequences.

On day one, laminin at a concentration of 25 µg/ml was dissolved in 0.1M NaHCO$_3$ (pH8.6) and then the solution was boiled for 15 minutes, thereby yielding thermally denatured laminin. Next, the solution was cooled to room temperature.

100 microliters of native laminin (unboiled) was added to four wells (Nunc-Immuno™ Maxisorp™ available from Nalge Nunc International, Rochester, N.Y.) and 100 microliters of denatured laminin (boiled) was added to a fifth well. The plate was swirled repeatedly until its surface was wet. The plate, with its top sealed, was incubated overnight at a temperature of 4° C. with a gentle agitation.

On day two, 10 ml of LB/tet medium was inoculated with a single colony of ER2738 *E. coli* strain. LB/tet medium was prepared as follows: A liter of LB medium was prepared from 10 g/l of Bacto-tryptone and 5 g/l NaCl. The mixture was autoclaved for 15 minutes at 121° C. and then stored at room temperature. Tetracycline stock was prepared using 20 mg/ml of tetracycline in ethanol, which was stored at minus 20° C. in the dark, and then vortexed prior to use. LB/tet plates were prepared from LB medium and 15 g/l agar, which was autoclaved for 15 minutes at 121° C. and cooled to less than 70° C. One ml of tetracycline stock was then added and the mixture was poured onto the plates. The plates were stored at 4° C. in the dark.

Coating solution was poured off the first well and the well was washed twice with TBST (TBS+0.1% (v/v) Tween-20). TBS was prepared from 50 mM Tris-HCl (pH 7.5) and 150 mM NaCl, which was autoclaved for 15 minutes at 121° C. and stored at room temperature.

Next, 2×10$^{11}$ phage (10 microliter of the original library, obtained from New England Bio Labs, Inc.) was diluted with 100 microliters of TBST and pipetted onto the first well. The first well was then rocked gently for 60 minutes at 4° C.

The coating solution of the second well was poured off and the well was washed twice with TBST. Supernatant from the first well was then pipetted onto the second well. The second well was rocked gently for 60 minutes at 4° C.

The coating solution of the third well was poured off and the well was washed twice with TBST. Supernatant from the second well was then pipetted onto the third well. The third well was rocked gently for 60 minutes at 4° C.

The coating solution of the fourth well was poured off and the well was washed twice with TBST. Supernatant from the third well was then pipetted onto the fourth well. The fourth well was rocked gently for 60 minutes at 4° C.

The coating solution of the fifth well was poured off and the well was filled with blocking buffer (0.1M NaHCO$_3$ (pH 8.6), 5 mg/ml BSA, 0.02% NaN3, filter sterilized and stored at 4° C.). Next, the fifth well was incubated for 60 minutes at 4° C. The blocking buffer solution was then discarded and the fifth well was washed six times with TBST. Supernatant from the fourth well was then pipetted onto the fifth well and the fifth well was incubated for 60 minutes at room temperature. Next, the solution was poured off the fifth well and the fifth well was washed ten times with TBST.

The phage bound to the fifth plate was eluted with 0.2M glycine-HCl (pH 2.2). Following elution, the phage was amplified and titrated. The phage was then used for the next round of panning. The process of day two was repeated three times, each time using the phage produced at the end of the previous run.

The final step was isolation and identification of the peptides by DNA sequencing, which yielded STQ-peptides.

Example 2

Peptide Antagonists of Denatured Laminin Blocked Retinal Pigmented Epithelial (RPE) Cell Adhesion to Denatured Laminin In vitro cell adhesion assays were conducted to determine whether the STQ-peptides bind to functional epitopes within denatured laminin that regulate cellular adhesion. Non-tissue culture treated 48-well plates were coated with denatured laminin. Human RPE cells were allowed to attach to the coated wells in the absence of STQ-peptide, in the presence of STQ-peptide at a concentration of 100 µg/ml, and in the presence of STQ-peptide at a concentration of 200 µg/ml.

Human denatured laminin (25 µg/ml) was immobilized on 48-well non-tissue culture treated plates. Wells were washed and incubated with 1% BSA (bovine serum albumin) in PBS (phosphate-buffered saline) for one hour at 37° C. Subconfluent RPE cells were harvested, washed, and resuspended in adhesion buffer containing RPMI-1640 medium, 1 mM MgCl$_2$, 0.2 mM MnCl$_2$, and 0.5% BSA. RPE cells (10$^5$) were resuspended in 200 µl of the adhesion buffer in the presence or absence of STQ-peptide at a concentration of 100 µg/ml or 200 µg/ml, and were added to each well and allowed to attach for 30 minutes at 37° C. The unattached cells were removed and the attached cells were stained for 10 minutes with crystal violet as described by Petitclerc, et al., Cancer Res. 1999; 59:2724-2730. The wells were washed three times with PBS and cell-associated crystal violet was eluted by addition of 100 µl of 10% acetic acid. Cell adhesion was quantified by measuring the optical density of eluted crystal violet at a wavelength of 600 nm.

The presence of STQ-peptide at either 100 µg/ml or 200 µg/ml resulted in a greater than 95% blockade of RPE cell adhesion to denatured laminin (FIG. 1).

Example 3

STQ-Peptide-S Blocked Melanoma Cell Adhesion to Denatured Laminin

Figure 2:
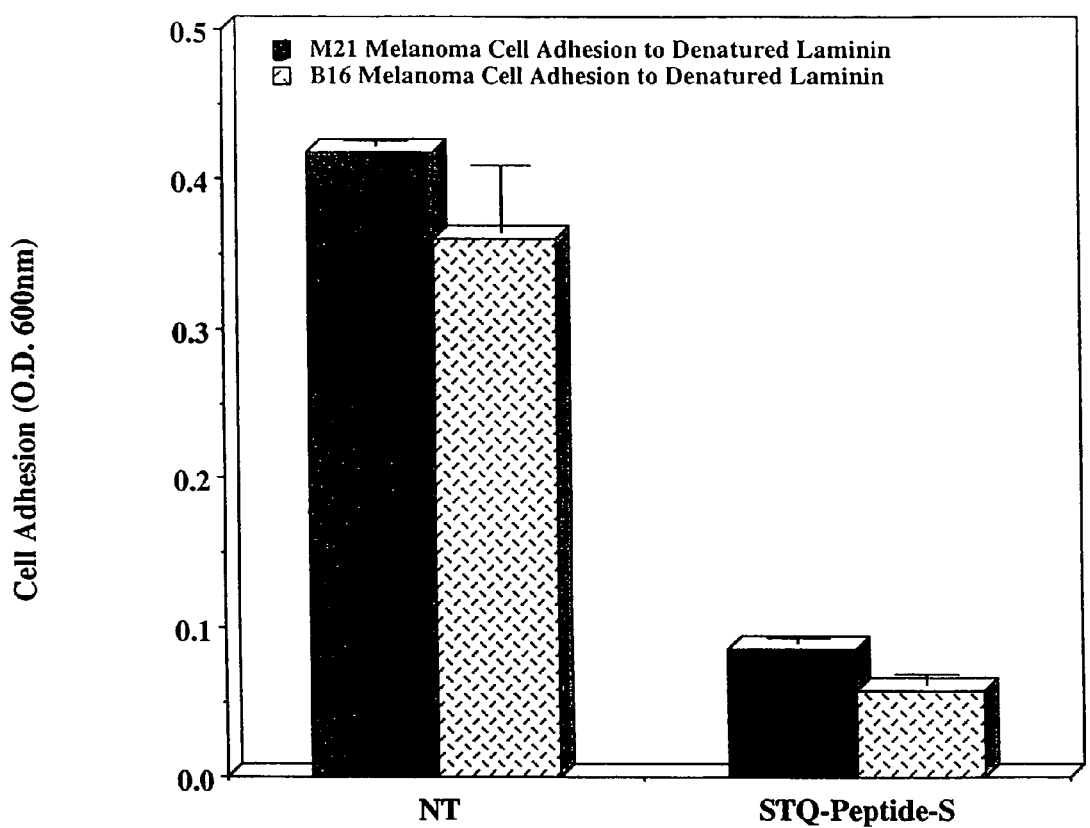
FIG. 2 is a chart which illustrates M21 human melanoma cell and B16 murine melanoma cell adhesion to untreated denatured laminin (NT) and STQ-peptide-S treated denatured laminin.

An adhesion assay was performed according to the method described in Example 2 and by Petticlerc, et al., Cancer Res. 1999; 59:2724-2730. Non-tissue culture treated 48-well plates were coated with denatured laminin in the absence of STQ-peptide-S and in the presence of STQ-peptide-S at a concentration of 50 µg/ml. Human M21 melanoma cells and murine B16 murine melanoma cells were allowed to attach to the coated wells. STQ-peptide-S blocked M21 and B16 melanoma cell adhesion by approximately 80% (FIG. 2).

Example 4

Figure 3:
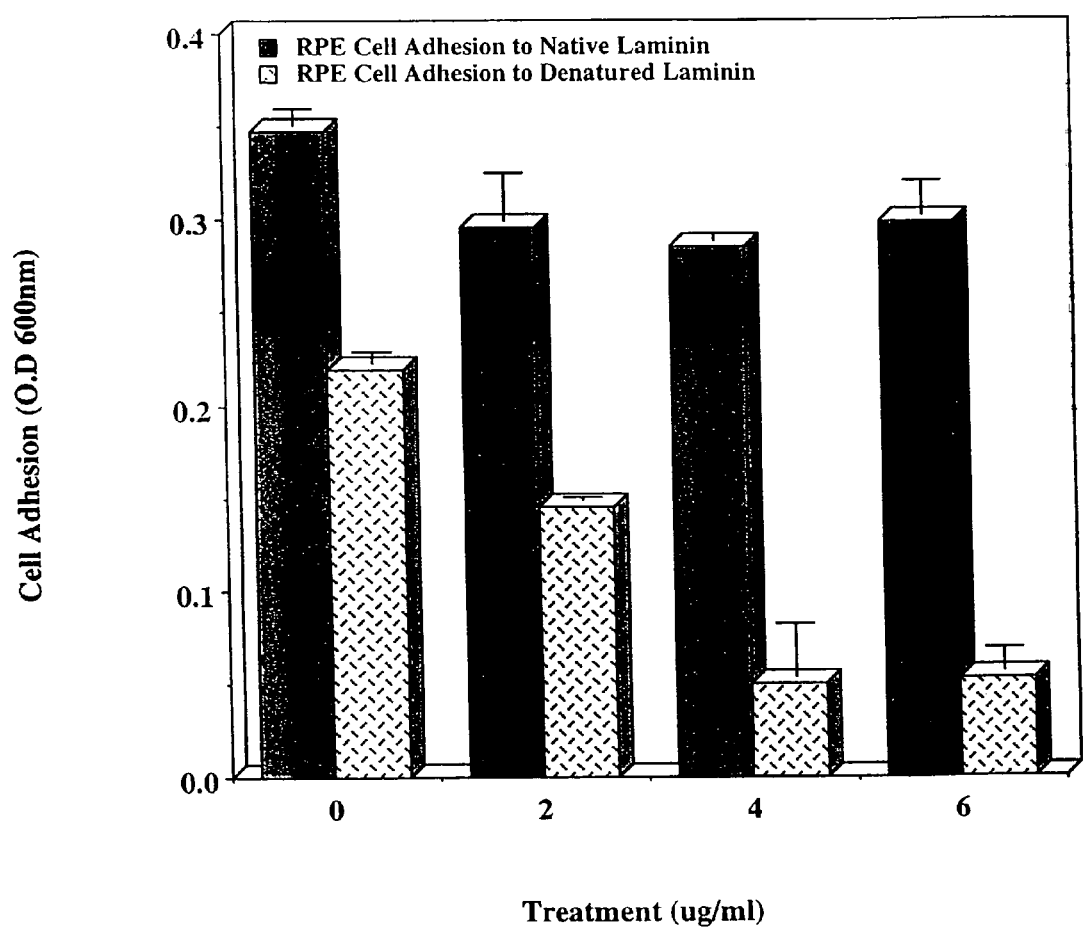
FIG. 3 is a chart which illustrates RPE cell adhesion to native laminin treated with different concentrations of STQ-peptide and denatured laminin treated with different concentrations of STQ-peptide.

Concentration Dependent Inhibition of RPE Cell Adhesion to Denatured Laminin by STQ-Peptide A set of non-tissue culture treated 48-well plates were coated with native laminin in the presence of different concentrations of STQ-peptide according to the method described in Example 2 and by Petticlerc, et al., Cancer Res. 1999; 59:2724-2730. Another set of non-tissue culture treated plates were coated with denatured laminin in the presence of different concentrations of STQ-peptide. STQ-peptide exhibited concentration dependent inhibition of RPE cell adhesion to the wells coated with denatured laminin. STQ-peptide had little effect on RPE cell adhesion to the wells coated with native laminin at any concentration of STQ-peptide tested (FIG. 3).

Example 5

STQ-Peptide Blocked bFGF-Induced Angiogenesis in the Chick CAM Model

Figure 4:
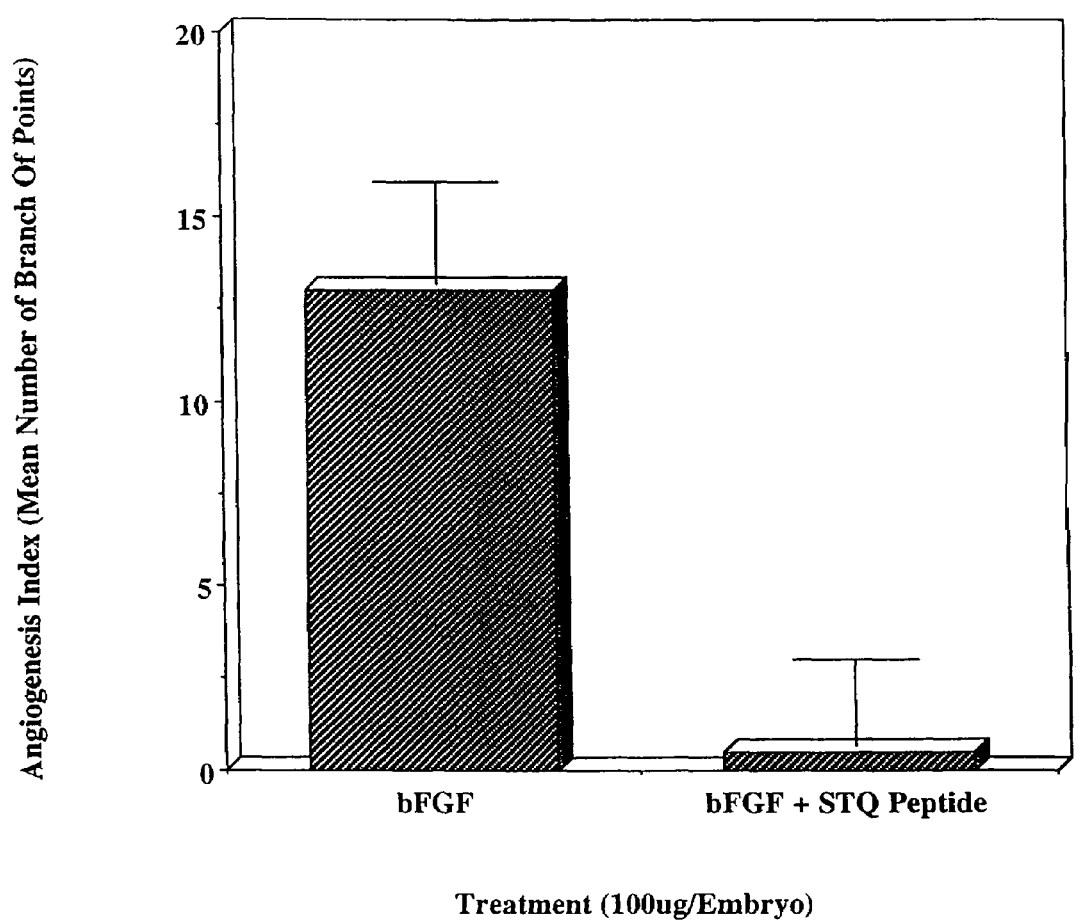
FIG. 4 is a chart which illustrates quantification of CAM angiogenic blood vessels following bFGF-induced angiogenesis without subsequent STQ-peptide treatment and CAM angiogenic blood vessels following bFGF-induced angiogenesis with subsequent STQ-peptide treatment.

Angiogenesis was induced within the chorioallantoic membrane (CAM) of 10-day old chick embryos with bFGF. Twenty-four hours later, 8-10 of the embryos were treated with a single intravenous injection of STQ-peptide (100 ug/embryo). At the end of a 3-day incubation period, the CAM tissues were removed for analysis. The injection of STQ-peptide resulted in a dramatic reduction in the number of branching vessels within the confined area of the filter disc. The single injection of STQ-peptide inhibited bFGF by greater than 95% (FIG. 4). No adverse effects were noted following injection of the peptide. Eight to ten chick embryos were tested in each of the two groups, and the experiment was repeated three times for a total of 24-30 chick embryos tested.

Example 6

STQ-Peptide Inhibited B16 Melanoma Metastasis In Vivo

Figure 5:
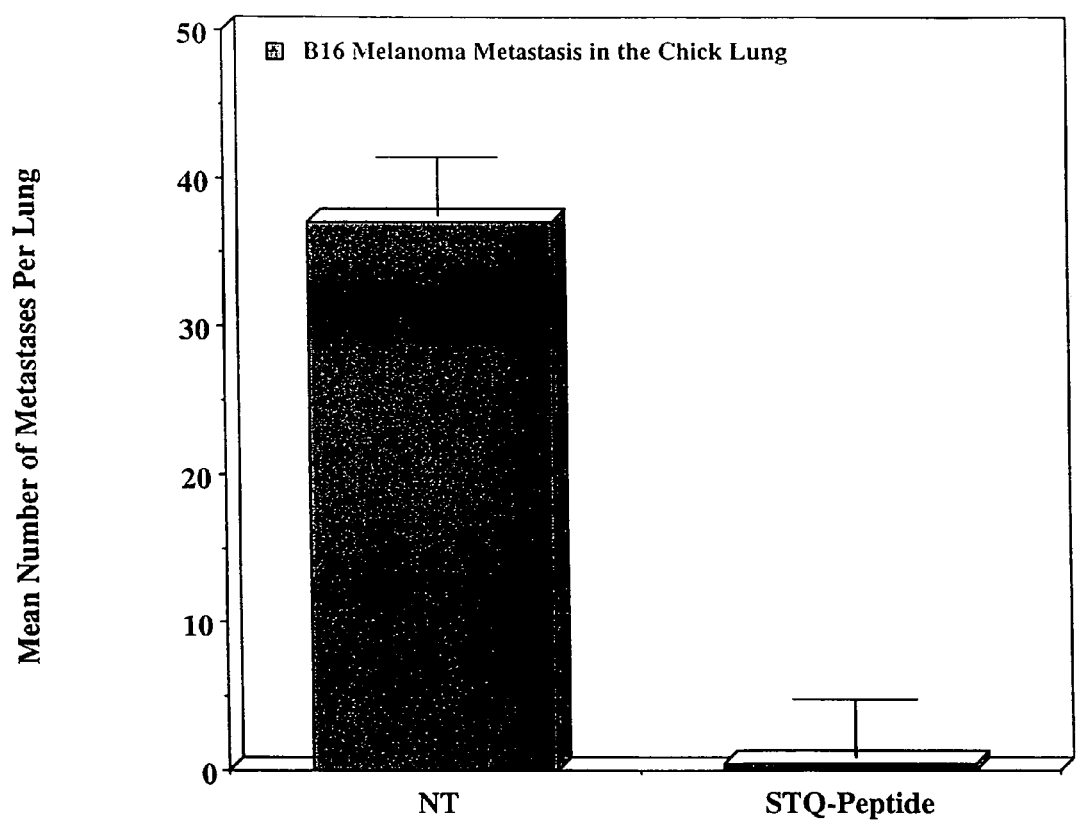
FIG. 5 is a chart which illustrates quantification of B16 melanoma metastases on chick embryo lungs untreated with STQ-peptide (NT) and chick embryo lungs treated with STQ-peptide.

Twelve-day old chick embryos (obtained from SPAFAS, North Franklin, Conn.) were injected intravenously with metastatic B16 melanoma cells (Chambers, et al., J. Natl. Cancer Inst. 1992; 84:797-803) in the presence or absence of STQ-peptide (100 ug/embryo). For each experiment, eight to ten chicks were tested under each set of conditions, and the experiment was repeated three times. The embryos were incubated for 7 days and then sacrificed. The chick lungs were analyzed for metastasis. B16 melanoma metastases appeared as discrete black lesions. The metastases were quantified by counting the B16 tumor lesions on the surface of the chick lungs for the STQ-peptide and no-STQ-peptide groups. B16 melanoma metastasis was inhibited by greater than 95% in the STQ-peptide group as compared to the no-STQ-peptide group (FIG. 5).

These results indicate that STQ-peptide is a powerful inhibitor of tumor metastasis in vivo.

Example 7

Treatment of a Patient with Metastatic Breast Cancer

A 60 kilogram patient with breast cancer metastatic to the liver has blood drawn for liver function tests. The patient undergoes an abdominal CT scan in order to note the size and number of the liver metastases. The patient's overall medical condition is assessed by a health professional using physical examination; blood tests such as a complete blood count, BUN, and creatinine; and EKG.

An STQ-peptide dose of 9000 milligrams is calculated by multiplying the patient's weight (60 kilograms) by the dose per body weight (150 milligrams per kilogram). The STQ-peptide dose is mixed in aqueous solution and administered intravenously through a peripheral vein catheter over a 2 hour period. Following infusion of STQ-peptide, the patient is monitored for 2 hours by a health professional for the appearance of adverse effects. In the absence of such effects, the patient is discharged home.

Two weeks following STQ-peptide infusion, the patient has repeat liver function tests and CT scan. Lowering of the liver function test values may be indicative of tumor metastases regression. CT scan visualization of decreased size and/or number of metastases is indicative of successful treatment of the metastases.

All patents and publications which are cited in the body of the instant specification are hereby incorporated by reference in their entirety.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

We claim:

1. A denatured laminin selective peptide antagonist comprising an amino acid sequence $NH_2$-S-T-Q-N-A-S-L-L-S-L-T-V-C-COOH (SEQ ID NO 1).

2. A denatured laminin selective peptide antagonist comprising an amino acid sequence $NH_2$-K-G-G-C-S-T-Q-N-A-Q-L-L-S-L-I-V-G-K-A-COOH (SEQ ID NO 2).

3. A denatured laminin selective peptide antagonist comprising an amino acid sequence $NH_2$-K-G-G-S-T-Q-N-A-Q-L-L-S-L-J-V-G-K-A-COOH (SEQ ID NO 3).

* * * * *